United States Patent
Descamps et al.

(10) Patent No.: US 11,590,108 B2
(45) Date of Patent: Feb. 28, 2023

(54) PHARMACEUTICAL COMPOSITIONS FOR COMBINATION THERAPY

(71) Applicant: Genfit, Loos (FR)

(72) Inventors: Emeline Descamps, Gondecourt (FR); Robert Walczak, Lille (FR); Carole Belanger, Bondues (FR); Benoît Noel, Gondecourt (FR)

(73) Assignee: Genfit, Loos (FR)

( * ) Notice: Subject to any disclaimer, the term of this patent is extended or adjusted under 35 U.S.C. 154(b) by 0 days.

(21) Appl. No.: 16/485,025

(22) PCT Filed: Feb. 23, 2018

(86) PCT No.: PCT/EP2018/054588
§ 371 (c)(1),
(2) Date: Aug. 9, 2019

(87) PCT Pub. No.: WO2018/154081
PCT Pub. Date: Aug. 30, 2018

(65) Prior Publication Data
US 2019/0388394 A1 Dec. 26, 2019

(30) Foreign Application Priority Data
Feb. 24, 2017 (EP) .................................. 17305213

(51) Int. Cl.
*A61K 31/4178* (2006.01)
*A61P 1/16* (2006.01)
*A61K 31/192* (2006.01)
*A61K 45/06* (2006.01)

(52) U.S. Cl.
CPC ........ *A61K 31/4178* (2013.01); *A61K 31/192* (2013.01); *A61P 1/16* (2018.01); *A61K 45/06* (2013.01)

(58) Field of Classification Search
CPC ...... A61K 31/192; A61K 31/4178; A61P 1/16
See application file for complete search history.

(56) References Cited

FOREIGN PATENT DOCUMENTS

| WO | WO-2011/064350 A1 | 6/2011 | |
|---|---|---|---|
| WO | WO-2016/040860 A1 | 3/2016 | |
| WO | WO-2017/048322 A1 | 3/2017 | |
| WO | WO-2017167935 A1 * | 10/2017 | ............ A61K 31/192 |
| WO | WO-2018051230 A1 * | 3/2018 | ......... A61K 31/4162 |

OTHER PUBLICATIONS

CAS Registry record for Reg. No. 923978-27-2, also known as elafibranor and GFT-505, retrieved from STN on Apr. 20, 2021.*

* cited by examiner

*Primary Examiner* — Theodore R. Howell
(74) *Attorney, Agent, or Firm* — Cesari & McKenna, LLP (57) ABSTRACT

The present invention relates to a combination of active ingredients for use in the treatment of diseases.

8 Claims, 4 Drawing Sheets

Specification includes a Sequence Listing.

SEQUENCE LISTING

<160> NUMBER OF SEQ ID NOS: 18

<210> SEQ ID NO 1
<211> LENGTH: 20
<212> TYPE: DNA
<213> ORGANISM: artificial
<220> FEATURE:
<223> OTHER INFORMATION: primer

<400> SEQUENCE: 1
tatgactcca ctcacggcaa                    20

<210> SEQ ID NO 2
<211> LENGTH: 20
<212> TYPE: DNA
<213> ORGANISM: artificial
<220> FEATURE:
<223> OTHER INFORMATION: primer

<400> SEQUENCE: 2
tccacgacat actcagcacc                    20

```
<210> SEQ ID NO 3
<211> LENGTH: 20
<212> TYPE: DNA
<213> ORGANISM: artificial
<220> FEATURE:
<223> OTHER INFORMATION: primer

<400> SEQUENCE: 3
ctgacagagg caccactgaa                                               20

<210> SEQ ID NO 4
<211> LENGTH: 20
<212> TYPE: DNA
<213> ORGANISM: artificial
<220> FEATURE:
<223> OTHER INFORMATION: primer

<400> SEQUENCE: 4
catctccaga gtccagcaca                                               20

<210> SEQ ID NO 5
<211> LENGTH: 20
<212> TYPE: DNA
<213> ORGANISM: artificial
<220> FEATURE:
<223> OTHER INFORMATION: primer

<400> SEQUENCE: 5
aggcgaacaa ggtgacagag                                               20

<210> SEQ ID NO 6
<211> LENGTH: 19
<212> TYPE: DNA
<213> ORGANISM: artificial
<220> FEATURE:
<223> OTHER INFORMATION: primer

<400> SEQUENCE: 6
gccaggagaa ccagcagag                                                19

<210> SEQ ID NO 7
<211> LENGTH: 20
<212> TYPE: DNA
<213> ORGANISM: artificial
<220> FEATURE:
<223> OTHER INFORMATION: primer

<400> SEQUENCE: 7
attggaagcc gaggtcccag                                               20

<210> SEQ ID NO 8
<211> LENGTH: 20
<212> TYPE: DNA
<213> ORGANISM: artificial
<220> FEATURE:
<223> OTHER INFORMATION: primer

<400> SEQUENCE: 8
tttgccccca ggtatgccag                                               20

<210> SEQ ID NO 9
<211> LENGTH: 20
<212> TYPE: DNA
<213> ORGANISM: artificial
<220> FEATURE:
<223> OTHER INFORMATION: primer
```

```
<400> SEQUENCE: 9
ttgcttcagc tccacagaga                                              20

<210> SEQ ID NO 10
<211> LENGTH: 20
<212> TYPE: DNA
<213> ORGANISM: artificial
<220> FEATURE:
<223> OTHER INFORMATION: primer

<400> SEQUENCE: 10
tggttgtaga gggcaaggac                                              20

<210> SEQ ID NO 11
<211> LENGTH: 20
<212> TYPE: DNA
<213> ORGANISM: artificial
<220> FEATURE:
<223> OTHER INFORMATION: primer

<400> SEQUENCE: 11
attcaaggct gtgggaaatg                                              20

<210> SEQ ID NO 12
<211> LENGTH: 20
<212> TYPE: DNA
<213> ORGANISM: artificial
<220> FEATURE:
<223> OTHER INFORMATION: primer

<400> SEQUENCE: 12
ctcagagtac gccagggaac                                              20

<210> SEQ ID NO 13
<211> LENGTH: 20
<212> TYPE: DNA
<213> ORGANISM: artificial
<220> FEATURE:
<223> OTHER INFORMATION: primer

<400> SEQUENCE: 13
tccctaagct catcgcagac                                              20

<210> SEQ ID NO 14
<211> LENGTH: 20
<212> TYPE: DNA
<213> ORGANISM: artificial
<220> FEATURE:
<223> OTHER INFORMATION: primer

<400> SEQUENCE: 14
gcttccaaac ttcacgctct                                              20

<210> SEQ ID NO 15
<211> LENGTH: 20
<212> TYPE: DNA
<213> ORGANISM: artificial
<220> FEATURE:
<223> OTHER INFORMATION: primer

<400> SEQUENCE: 15
cgtggaactg gcagaagagg                                              20

<210> SEQ ID NO 16
```

```
<211> LENGTH: 20
<212> TYPE: DNA
<213> ORGANISM: artificial
<220> FEATURE:
<223> OTHER INFORMATION: primer

<400> SEQUENCE: 16
agacagaaga gcgtggtggc                                               20

<210> SEQ ID NO 17
<211> LENGTH: 20
<212> TYPE: DNA
<213> ORGANISM: artificial
<220> FEATURE:
<223> OTHER INFORMATION: primer

<400> SEQUENCE: 17
gcctgctgtt cacagttgcc                                               20

<210> SEQ ID NO 18
<211> LENGTH: 20
<212> TYPE: DNA
<213> ORGANISM: artificial
<220> FEATURE:
<223> OTHER INFORMATION: primer

<400> SEQUENCE: 18
ctttgggaca cctgctgctg                                               20
```

PHARMACEUTICAL COMPOSITIONS FOR COMBINATION THERAPY

CROSS-REFERENCE TO RELATED APPLICATIONS

This application is the National Stage of International Application No. PCT/EP2018/054588, filed Feb. 23, 2018, which claims priority to European Application No. 17305213.5, filed Feb. 24, 2017. The contents of both prior applications are hereby incorporated by reference herein in their entirety.

TECHNICAL FIELD

The present invention relates to pharmaceutical combinations containing a PPAR agonist and (S,E)-8-(4-(2-Butoxyethoxy)phenyl)-1-(2-methylpropyl)-N-(4-(((1-propyl-1H-imidazol-5-yl)methyl)sulfinyl)phenyl)-1,2,3,4-tetrahydrobenzo[b]azocine-5-carboxamide, also known as cenicriviroc (CVC), or its derivatives, and their use in combination therapy.

BACKGROUND

According to the Washington Manual of Medical Therapeutics (31st ed.; 2004; Lippincott Williams & Wilkins), liver disorders can be categorized in different groups of diseases, in particular viral diseases, drug- and alcohol-related liver diseases, immune-mediated liver diseases, metabolic liver diseases, miscellaneous diseases such as non-alcoholic fatty liver disease, and complications of hepatic insufficiency (such as fulminant hepatic failure or hepatocellular carcinoma).

In particular, non-alcoholic fatty liver disease (NAFLD) is a common hepatic disorder with histological features of alcohol-induced fatty liver disease in individuals who consume little or no alcohol (Yeh M et al., 2007; Marchesini G et al., 2003). NAFLD is due to the abnormal retention of lipids within cells (commonly defined as steatosis), an event more frequent in liver since this organ is primarily responsible of lipid metabolism. NAFLD has a spectrum of histological forms including hepatic steatosis, and non-alcoholic steatohepatitis (NASH), which is characterized by liver inflammation, steatosis, necrosis and fibrosis due to the disruption of liver cells. Conditions associated with NAFLD are varied, and include type 2 diabetes, obesity, dyslipidemia, metabolic syndrome, treatment with hepatotoxic drugs, toxins, infectious agents, or other exogenous causes.

Although NAFLD typically follows a benign, non-progressive clinical course, NASH is a potentially serious condition; as many as 25% of patients may progress to advanced fibrosis, cirrhosis and experience complications of portal hypertension, liver failure and hepatocellular carcinoma, which makes an early and correct assessment mandatory (Yeh M et al, 2007).

Means for an effective treatment for liver fibrotic diseases, and NAFLD and NASH in particular, are still insufficient. No treatment is established for patient with NASH, and several therapeutic options are tested in clinical trial (Vuppalanchi R and Chalasani N, 2009, Dowman J. K et al., 2009). These studies involve the use of many different families of chemical compounds (fibrates, thiazolidinediones, biguanides, statins, cannabinoids) and therapeutic targets (nuclear receptors, angiotensin receptors, cannabinoid receptors, HMG-CoA reductase). Recently, studies involving thiazolidinediones (Rosiglitazone and Pioglitazone) have shown that these drugs may improve liver condition but treatment with these drugs is not without undesired effects such as higher risks of congestive cardiac failure and osteoporosis, as well as weight gain with psychological effects on the patient (Dowman J. K et al., 2010; Shiri-Sverdlov R et al., 2006; Neuschwander-Tetri et al., 2003). Clinical trials involving the administration of cannabinoids have raised the concern of neuropsychiatric disruption (Vuppanchi R and Chalasani N, 2009). Other therapies currently ongoing are seeking to assess in NASH drugs as antioxidants but none of these treatments has yet showed convincing results (Nelson A et al., 2009).

Several compounds with different mechanisms of action are currently in Phase 2 or 3 clinical trials.

1-[4-methylthiophenyl]-3-[3,5-dimethyl-4-carboxydimethylmethyloxyphenyl]prop-2-en-1-one (Elafibranor, or ELA formerly named GFT505), a PPAR-alpha/delta dual agonist disclosed in WO2004005233, possesses properties which can be advantageous for the treatment of a number of diseases, including fibrotic disorders, gastroenterology diseases and liver diseases, in particular cholestatic diseases such as primary biliary cholangitic (PBC) and PSC (primary sclerosing cholangitis), or liver diseases, in particular non-alcoholic fatty liver diseases (NAFLD) such as non-alcoholic steatohepatitis (NASH). Elafibranor was evaluated for clinical efficacy in NASH in a one-year liver biopsy-based Phase 2b trial (GFT505-2127), one of the largest interventional studies ever conducted in NASH. Administered to over 800 patients and healthy volunteers to date, elafibranor has demonstrated beneficial properties for NASH, including in particular: improvement of markers of liver dysfunction, including ALAT, ASAT, γGT, ALP; improvement of insulin sensitivity and glucose homeostasis; favorable effects on plasma lipids, including decrease of plasma triglycerides and LDL-C, and increase of HDL-C levels; anti-inflammatory properties; efficacy on histological NASH parameters (steatosis, inflammation, fibrosis) in animal disease models—anti-fibrotic activities; and the absence of safety concern has been confirmed in a full toxicological package up to 2-year carcinogenicity studies. Elafibranor is currently being evaluated in a clinical phase 3 study for the treatment of NASH. Evaluation of this molecule for the treatment of PBC in a clinical phase 2 study has also started.

CVC, a dual CCR2/5 antagonist, is another compound which was proposed for the treatment of NASH or liver fibrosis. CVC was previously evaluated in the CENTAUR phase 2b study for the treatment of NASH in adult subjects with liver fibrosis, the primary outcome being defined by a minimum 2-point improvement in NAS with at least a 1-point reduction in either lobular inflammation or hepatocellular ballooning after one year of treatment with CVC 150 mg, administered orally once daily and taken every morning with food. However, the primary outcome was not met. During the study, data were generated showing a decrease of fibrosis in certain proportion of patients treated with CVC as compared to placebo. As a consequence, CVC is currently evaluated for the treatment of liver fibrosis in NASH patients in the AURORA phase 3 study, the primary endpoint at month 12 being the improvement in fibrosis by at least 1 stage (according to the NASH CRN system) and no worsening of steatohepatitis, and a superiority as compared to placebo on the composite endpoint of histopathologic progression to cirrhosis, liver-related clinical outcomes, and all-cause mortality.

Several mechanisms are responsible for the development of NASH, but no information is available providing an insight on what combinations of products would be effective in improving NASH therapy. The present invention relates to such an unexpected improvement.

SUMMARY OF INVENTION

The present invention relates to a combination product comprising:
(i) CVC or an analogue, a pharmaceutically acceptable salt or a solvate thereof, and
(ii) at least one PPAR agonist of formula (I), in which:
Y1 represents a halogen, a Ra, or Ga—Ra group;
A represents a CH=CH or a CH2-CH2 group;
Y2 represents a Gb-Rb group;
Ga and Gb, identical or different, represent an atom of oxygen or sulfur;
Ra represents a hydrogen atom, an unsubstituted (C1-C6) alkyl group, a (C6-C14)aryl group or a (C1-C6)alkyl group that is substituted by one or more halogen atoms, a (C1-C6)alkoxy or a (C1-C6)alkylthio group, (C3-C14)cycloalkyl groups, (C3-C14)cycloalkylthio groups or heterocyclic groups;
Rb represents a (C1-C6)alkyl group substituted by at least a —COORc group, wherein
Rc represents a hydrogen atom, or a (C1-C6)alkyl group that is substituted or not by
one or more halogen atoms, (C3-C14)cycloalkyl groups, or heterocyclic groups; and
Y4 and Y5, identical or different, representing a (C1-C6) alkyl group that is substituted or not by one or more halogen atoms, (C3-C14)cycloalkyl groups or heterocyclic groups.

In a particular embodiment, component (i) of the combination is CVC or a pharmaceutically acceptable salt thereof.

In a particular embodiment, the at least one PPAR agonist is 1-[4-methylthiophenyl]-3-[3,5-dimethyl-4-carboxydimethylmethyloxyphenyl]prop-2-en-1-one (Elafibranor, or ELA formerly named GFT505).

According to a preferred embodiment of the present invention, the combination product of the invention comprises CVC and Elafibranor.

Furthermore, the combination product of the invention may further comprise at least one therapeutically active agent with known antifibrotic activity selected from pirfenidone or receptor tyrosine kinase inhibitors (RTKIs) such as Nintedanib, Sorafenib and other RTKIs, or angiotensin II (AT1) receptor blockers, or CTGF inhibitor, or any antifibrotic compound susceptible to interfere with the TGFβ and BMP-activated pathways including activators of the latent TGFβ complex such as MMP2, MMP9, THBS1 or cell-surface integrins, TGFβ receptors type I (TGFBRI) or type II (TGFBRII) and their ligands such as TGFβ, Activin, inhibin, Nodal, anti-MOllerian hormone, GDFs or BMPs, auxiliary co-receptors (also known as type III receptors), or components of the SMAD-dependent canonical pathway including regulatory or inhibitory SMAD proteins, or members of the SMAD-independent or non-canonical pathways including various branches of MAPK signaling, TAK1, Rho-like GTPase signaling pathways, phosphatidylinositol-3 kinase/AKT pathways, TGFβ-induced EMT process, or canonical and non-canonical Hedgehog signaling pathways including Hh ligands or target genes, or any members of the WNT, or Notch pathways which are susceptible to influence TGFβ.

Alternatively, the combination product according to the invention may further comprise at least one therapeutically active agent selected from JAK/STAT inhibitors and other anti-inflammatory and/or immunosuppressant agents. For example, the therapeutically active agent may be selected from glucocorticoids, NSAIDS, cyclophosphamide, nitrosoureas, folic acid analogs, purine analogs, pyrimidine analogs, methotrexate, azathioprine, mercaptopurine, ciclosporin, myriocin, tacrolimus, sirolimus, mycophenolic acid derivatives, fingolimod and other sphingosine-1-phosphate receptor modulators, monoclonal and/or polyclonal antibodies against such targets as proinflammatory cytokines and proinflammatory cytokine receptors, T-cell receptor and integrins.

The combination product of the invention may be in the form of a pharmaceutical composition or of a kit-of-parts. The components of the combination of the invention, when in the form of a kit of parts, may be administered simultaneously, sequentially and separately.

The present invention also relates to the therapeutic use of the combination product of the present invention. As such, the invention also relates to the combination product disclosed herein, for use as a medicament.

The combination product of the invention is useful, in particular, for treating or preventing diseases such as immune (e.g. autoimmune), inflammatory, metabolic, fibrotic and cholestatic diseases. Accordingly, the invention relates to the combination product of the invention, for use in a method for the treatment of an immune (e.g. autoimmune), inflammatory, metabolic, fibrotic or cholestatic disease. The invention further relates to the use of a combination product of the invention in the manufacture of a medicament for the treatment of an immune (e.g. autoimmune), inflammatory, metabolic, fibrotic or cholestatic disease. The invention further relates to a method for the treatment of an immune (e.g. autoimmune), inflammatory, metabolic, fibrotic or cholestatic disease in a patient in need thereof, comprising administering to said subject a therapeutically effective amount of the combination product of the invention.

In a particular embodiment, the disease is selected in the group consisting of metabolic liver diseases, non-alcoholic fatty liver disease (NAFLD), non-alcoholic steatohepatitis (NASH), drug-induced liver diseases, alcohol-induced liver diseases, infectious agent induced liver diseases, inflammatory liver diseases, immune system dysfunction-mediated liver diseases, dyslipidemia, cardiovascular diseases, restenosis, syndrome X, metabolic syndrome, diabetes, obesity, hypertension, chronic cholangiopathies such as Primary Sclerosing Cholangitis (PSC), Primary Biliary Cholangitis (PBC), biliary atresia, familial intrahepatic cholestasis type 3 (PFIC3), inflammatory bowel diseases, Crohn's disease, ulcerative colitis, keloid, old myocardial infarction, scleroderma/systemic sclerosis, inflammatory diseases, neurodegenerative diseases, cancers, liver cancer, hepatocallular carcinoma, gastrointestinal cancer, gastric cancer, meningioma associated with neurofibromatosis, pancreatic neuroendocrine tumors, pancreatic exocrine tumors, leukemia, myeloproliferative/myelodysplastic diseases, mastocytosis, dermatofibrosarcoma, solid tumors including breast, lung, thyroid or colorectal cancer, a prostate cancer, liver fibrosis or cirrhosis of any origin, metabolic disease-induced liver fibrosis or cirrhosis, NAFLD-induced fibrosis or cirrhosis, NASH-induced fibrosis or cirrhosis, alcohol-induced liver fibrosis or cirrhosis, drug-induced liver fibrosis or cirrhosis, infectious agent-induced liver fibrosis or cirrhosis, parasite infection-induced liver fibrosis or cirrhosis, bacterial infection-induced liver fibrosis or cirrhosis, viral infection-induced fibrosis or cirrhosis, HBV-infection induced liver fibrosis or cirrhosis, HCV-infection induced liver fibrosis or cirrhosis, HIV-infection induced liver fibrosis or cirrhosis, dual HCV and HIV-infection induced liver fibrosis or cirrhosis, radiation- or chemotherapy-induced fibrosis or cirrhosis, biliary tract fibrosis, liver fibrosis or cirrhosis due to any chronic cholestatic disease, gut fibrosis of any etiology, Crohn's disease-induced fibrosis, ulcerative colitis-induced fibrosis, intestine (e.g. small intestine) fibrosis, colon fibrosis, stomach fibrosis, skin fibrosis, epidermis fibrosis, endodermis fibrosis, skin fibrosis due to scleroderma/systemic sclerosis, lung fibrosis, lung fibrosis consecutive to chronic inflammatory airway diseases, such as COPD, asthma, emphysema, smoker's lung, tuberculosis, pulmonary fibrosis, idiopathic pulmonary fibrosis (IPF), heart fibrosis, kidney fibrosis, nephrogenic systemic fibrosis, muscle fibrosis, soft tissue (e.g. mediastinum or retroperitoneum) fibrosis, bone marrow fibrosis, joint fibrosis, tendon fibrosis, cartilage fibrosis, pancreas fibrosis, uterus fibrosis, nervous system fibrosis, testis fibrosis, ovary fibrosis, adrenal gland fibrosis, artery fibrosis, vein fibrosis, eye fibrosis, endomyocardial fibrosis, mediastinal fibrosis, myelofibrosis, retroperitoneal fibrosis, progressive massive fibrosis (a complication of coal workers' pneumoconiosis), proliferative fibrosis, neoplastic fibrosis, peri-implantational fibrosis and asbestosis, arthrofibrosis, adhesive capsulitis.

In a further particular embodiment, the disease is selected in the group consisting of metabolic liver diseases, non-alcoholic fatty liver disease (NAFLD), non-alcoholic steatohepatitis (NASH), drug-induced liver diseases, alcohol-induced liver diseases, infectious agent induced liver diseases, inflammatory liver diseases, immune system dysfunction-mediated liver diseases, dyslipidemia, cardiovascular diseases, restenosis, syndrome X, metabolic syndrome, diabetes, obesity, hypertension, chronic cholangiopathies such as Primary Sclerosing Cholangitis (PSC), Primary Biliary Cholangitis (PBC), biliary atresia, familial intrahepatic cholestasis type 3 (PFIC3), inflammatory bowel diseases, Crohn's disease, ulcerative colitis, liver cancer, hepatocallular carcinoma, gastrointestinal cancer, gastric cancer, colorectal cancer, metabolic disease-induced liver fibrosis or cirrhosis, NAFLD-induced fibrosis or cirrhosis, NASH-induced fibrosis or cirrhosis, alcohol-induced liver fibrosis or cirrhosis, drug-induced liver fibrosis or cirrhosis, infectious agent-induced liver fibrosis or cirrhosis, parasite infection-induced liver fibrosis or cirrhosis, bacterial infection-induced liver fibrosis or cirrhosis, viral infection-induced fibrosis or cirrhosis, HBV-infection induced liver fibrosis or cirrhosis, HCV-infection induced liver fibrosis or cirrhosis, HIV-infection induced liver fibrosis or cirrhosis, dual HCV and HIV-infection induced liver fibrosis or cirrhosis, radiation- or chemotherapy-induced fibrosis or cirrhosis, biliary tract fibrosis, liver fibrosis or cirrhosis due to any chronic cholestatic disease, gut fibrosis of any etiology, Crohn's disease-induced fibrosis, ulcerative colitis-induced fibrosis, intestine (e.g. small intestine) fibrosis, colon fibrosis, stomach fibrosis, lung fibrosis, lung fibrosis consecutive to chronic inflammatory airway diseases, such as COPD, asthma, emphysema, smoker's lung, tuberculosis, pulmonary fibrosis, idiopathic pulmonary fibrosis (IPF).

The compositions and methods of the present invention address unmet needs in the treatment or prevention of such diseases.

DESCRIPTION OF THE FIGURES AND TABLES

Abbreviations used in the figures, in the tables, and in the text:
α-SMA: alpha Smooth Muscle Actin
BMP: Bone Morphogenetic Protein
cDNA: Complementary Deoxyribonucleotide acid
COL1A1: Collagen, type 1, Alpha 1
CDAA: Choline-Deficient L-Amino Acid
CSAA: Choline Supplemented L-Amino Acid-defined
CVC: Cenicriviroc
DMSO: Dimethyl sulfoxide
DNA: Desoxyribonucleic Acid
DTT: Dithiothreitol
ELA: Elafibranor or GFT 505
ELISA: Enzyme-Linked Immunosorbent Assay
EMT: Epithelial-mesenchymal transition
EOB: Excess Over Bliss
FBS: Fetal Bovine Serum
FDA: Food and Drug Administration
FPP: Farnesyl Pyrophosphate
GDF: Growth Differentiation Factors
Hh: Hedgehog
GGPP: Geranylgeranlpyrophosphate
HMG-CoA: 3-hydroxy-3-méthylglutaryl-coenzyme A
hHSC: Human Hepatic Stellate Cells
HSC: Hepatic Stellate Cells
$IC_{50}$: Half maximal Inhibitory Concentration
InMyoFib: Intestinal Myofibroblasts
LBD: Ligand Binding Domain
MMP2: Matrix Metallopeptidase 2
MMP9: Matrix Metallopeptidase 9
µl: microliter
LDL: Low Density Lipoprotein
NHLF: Normal Human Lung Fibroblasts
PBS: Phosphate Buffer Saline
PFOR: Pyruvate Ferredoxin Oxidoreductase
PPAR: Peroxisome Proliferator Activated Receptor
PPRE: PPAR Response Elements
qPCR: Quantitative Polymerase Chain Reaction
pMol: picomoles
rhFGF: recombinant human basic Fibroblast Growth Factor
RNA: Ribonucleic Acid
RT: Reverse Transcriptase
SmBM: Smooth Muscle cell Basal Medium
SteCGS: Stellate Cell Growth Supplement
STeCM: Stellate Cell Medium
TGFβ1: Tumor Growth Factor beta 1
TGFBRI: TGFβ type I receptor
TGFBRII: TGFβ type II receptor
THBS1: Thrombospondine 1
TMB: Tetramethylbenzidine

After 48 hours of incubation, the expression of α-SMA was measured by ELISA.

The obtained values were transformed into percentage inhibition over TGFβ1 control. Data are presented as mean (quadruplicates)±standard deviation (SD). Statistical analyses were performed by one-way ANOVA followed by Bonferroni post-hoc tests, using Sigma Plot 11.0 software. [*: $p<0.05$; : $p<0.01$; *: $p<0.001$ (comparison versus TGFβ1 1 ng/mL group)]. The curve fitting and the calculation of half maximal inhibitory concentration ($IC_{50}$) were performed with XLFit software 5.3.1.3.

(A) Percentage of α-SMA inhibition over the TGFβ1 control for all combination pairs. Data are presented as mean of quadruplicates.

(B) EOB scores were calculated as described in Materials and Methods. Any compound pair with EOB values>10 was considered synergistic (colored from light grey to black). The total EOB score including all combinations was also calculated.

(C) Data values derived from a synergistic combination pair were plotted in a bar graph representation. Data are presented as mean (quadruplicates)±standard deviation (SD). *: $p<0.05$; : $p<0.01$; *: $p<0.001$ using a student's t-test to compare the combination group over the highest single agent.

Disease activity was assessed by the NAS score (sum of the grades of steatosis, ballooning and lobular inflammation) (A). Liver damages were assessed by (B) plasma CK18-M30 concentration (marker of apoptosis) and plasma AST (C) concentrations (markers of cytolysis). Data are expressed as mean±SD. § $p<0.05$, §§ $p<0.01$, § § § $p<0.001$ using Kruskal-Wallis and uncorrected Dunn's post-hoc test. ¤ $p<0.05$, ¤¤ $p<0.01$, ¤¤¤ $p<0.001$, using Student unilateral t-test with Welsh correction. HSA, Highest Single Agent model.

Expression of α-SMA, TGFβ1, Col1α1, Col1α2 (fibrogenesis) TIMP1 and MMP2 (tissue remodeling) and TNFα and MCP1 (inflammation) was assessed by real time quantitative PCR. Data are expressed as mean±SD. ¤ $p<0.05$, ¤¤ $p<0.01$, ¤¤¤ $p<0.001$ using Student unilateral t-test with Welsh correction. HSA, Highest Single Agent model.

DETAILED DESCRIPTION OF THE INVENTION

It is to be understood that this invention is not limited to the specific products, methods, conditions or parameters described and/or shown herein, and that the terminology used herein is for the purpose of describing particular embodiments by way of examples only and is not intended to limit the claimed invention.

Unless defined otherwise, all technical and scientific terms used herein have the same meaning as is commonly understood by one of skill in the art to which the present disclosure belongs.

The following terms and abbreviations, unless otherwise indicated, shall be understood to have the following meanings.

In the present disclosure, the singular forms "a", "an" and "the" include the plural reference, and reference to a particular numerical value includes at least that particular value, unless the context clearly indicates otherwise. Thus, for example, a reference to "a solvent" is a reference to one or more of such solvents and equivalents thereof to those skilled in the art, and so forth.

As used above, the term "disease" refers to a disease, disorder, condition, symptom, or indication. This term is used interchangeably with the phrase "disease or disorder".

As used herein, the terms "treatment" or "therapy" (as well as different word forms thereof) includes preventative (e.g., prophylactic), curative, or palliative treatment. Such preventative, curative, or palliative treatment may be full or partial. For example, complete elimination of unwanted symptoms, or partial elimination of one or more unwanted symptoms would represent "treatment" as contemplated herein.

As employed above and throughout the disclosure the term "therapeutically effective amount" refers to an amount effective, at dosages, and for periods of time necessary, to achieve the desired result with respect to the treatment of the relevant disorder, condition, or side effect. It will be appreciated that the effective amount of components of the present invention will vary from patient to patient not only with the particular compound, component or composition selected, the route of administration, and the ability of the components to elicit a desired response in the individual, but also with factors such as the disease state or severity of the condition to be alleviated, hormone levels, age, sex, weight of the individual, the state of being of the patient, and the severity of the condition being treated, concurrent medication or special diets then being followed by the particular patient, and other factors which those skilled in the art will recognize, with the appropriate dosage ultimately being at the discretion of the attendant physician. Dosage regimens may be adjusted to provide the improved therapeutic response. An effective amount is also one in which any toxic or detrimental effects of the components are outweighed by the therapeutically beneficial effects.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

"Salt" and "pharmaceutically acceptable salt" includes both acid and base addition salts. "Acid addition salt" refers to those salts that retain the biological effectiveness and properties of the free bases, which are not biologically or otherwise undesirable, and which are formed with inorganic acids and organic acids. "Base addition salt" refers to those salts that retain the biological effectiveness and properties of the free acids, which are not biologically or otherwise undesirable, and which are prepared from addition of an inorganic base or an organic base to the free acid. Examples of pharmaceutically acceptable salts include, but are not limited to, mineral or organic acid addition salts of basic residues such as amines; alkali or organic addition salts of acidic residues; and the like, or a combination comprising one or more of the foregoing salts. The pharmaceutically acceptable salts include salts and the quaternary ammonium salts of the active agent. For example, acid salts include those derived from inorganic acids such as hydrochloric, hydrobromic, sulfuric, sulfamic, phosphoric, nitric and the like; other acceptable inorganic salts include metal salts such as sodium salt, potassium salt, cesium salt, and the like; and alkaline earth metal salts, such as calcium salt, magnesium salt, and the like, or a combination comprising one or more of the foregoing salts. Pharmaceutically acceptable organic salts includes salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—(CH2)n-COOH where n is 0-4, and the like; organic amine salts such as triethylamine salt, pyridine salt, picoline salt, ethanolamine salt, triethanolamine salt, dicyclohexylamine salt, N,N'-dibenzylethylenediamine salt, and the like; and amino acid salts such as arginate, aspartginate, glutamate, and the like; or a combination comprising one or more of the foregoing salts.

"Solvate" means a complex formed by solvation (the combination of solvent molecules with molecules or ions of an active agent implemented in the present invention), or an aggregate that consists of a solute ion or molecule (an active agent implemented in the present invention) with one or more solvent molecules. In the present invention, the preferred solvate is hydrate.

"Pharmaceutical composition" refers to a formulation of a compound of the present disclosure and a medium generally accepted in the art for the delivery of the biologically active compound to mammals, e.g., humans. Such a medium includes all pharmaceutically acceptable carriers, diluents or excipients therefore.

"Administering" includes any mode of administration, such as oral, subcutaneous, sublingual, transmucosal, parenteral, intravenous, intra-arterial, buccal, sublingual, topical, vaginal, rectal, ophthalmic, otic, nasal, inhaled, intramuscular, intraosseous, intrathecal, and transdermal, or a combination thereof. "Administering" can also include prescribing or filling a prescription for a dosage form comprising a particular compound. "Administering" can also include providing directions to carry out a method involving a particular compound or a dosage form comprising the compound.

The present invention relates to a combination product comprising (i) at least CVC or a derivative, or an analogue, or a pharmaceutically acceptable salt or solvate thereof, (ii) at least a PPAR agonist of formula (I)

in which:
Y1 represents a halogen, a Ra, or Ga—Ra group;
A represents a CH=CH or a CH2-CH2 group;
Y2 represents a Gb-Rb group;
Ga and Gb, identical or different, represent an atom of oxygen or sulfur;
Ra represents a hydrogen atom, an unsubstituted (C1-C6) alkyl group, a (C6-C14)aryl group or a (C1-C6)alkyl group that is substituted by one or more halogen atoms, a (C1-C6)alkoxy or a (C1-C6)alkylthio group, (C3-C14)cycloalkyl groups, (C3-C14)cycloalkylthio groups or heterocyclic groups;
Rb represents a (C1-C6)alkyl group substituted by at least a —COORc group, wherein Rc represents a hydrogen atom, or a (C1-C6)alkyl group that is substituted or not by one or more halogen atoms, (C3-C14)cycloalkyl groups, or heterocyclic groups; and
Y4 and Y5, identical or different, representing a (C1-C6) alkyl group that is substituted or not by one or more halogen atoms, (C3-C14)cycloalkyl groups or heterocyclic groups.

In a particular embodiment of the compound of formula (I):
Y1 represents a halogen, a Ra, or a Ga—Ra group;
A represents a CH=CH group;
Y2 represents a Gb-Rb group;
Ga and Gb, identical or different, represent an atom of oxygen or sulfur;
Ra represents a (C1-C6)alkyl or (C3-C14)cycloalkyl group, in particular a (C1-C7)alkyl or (C3-C14)cycloalkyl group substituted or not by one or more halogen atoms;
Rb represents a (C1-C6)alkyl group substituted by a —COOR3 group, wherein Rc represents a hydrogen atom or an alkyl group having from one to four carbon atoms; and
Y4 and Y5 independently represent a (C1-C4)alkyl group.

In a particular embodiment of the compound of formula (I):
Y1 represents a Ra or Ga—Ra group;
A represents a CH2-CH2 group;
Y2 represents a Gb-Rb group;
Ga represents an atom of oxygen or sulfur and Gb represents an atom of oxygen;
Ra represents a (C1-C6)alkyl or (C3-C7)cycloalkyl group;
Rb represents a (C1-C6)alkyl group substituted by at least a —COORc group, wherein Rc represents a hydrogen atom or (C1-C4)alkyl group; and
Y4 and Y5 independently represent a (C1-C4)alkyl group.

In a particular embodiment of the compound of formula (I):
Y1 represents a halogen atom or a Ra or Ga—Ra group;
A represents a CH2-CH2 group;
Y2 represents a Gb-Rb group;
Ga represents an atom of oxygen or sulfur and Gb represents an atom of oxygen;
Ra represents a (C1-C6)alkyl or (C3-C14)cycloalkyl group that is substituted by one or more halogen atoms;
Rb represents a (C1-C6)alkyl group substituted or not by one or more halogen atoms and substituted by at least a —COORc group, wherein Rc represents a hydrogen atom or a (C1-C4)alkyl group; and
Y4 and Y5 represent a (C1-C4)alkyl group.

In a particular embodiment of the compound of formula (I), Gb is an oxygen atom and Rb is (C1-C6)alkyl group substituted by a —COORc group, wherein Rc represents a hydrogen atom or an unsubstituted linear or branched (C1-C4)alkyl group.

In a particular embodiment of the compound of formula (I), Y1 is a (C1-C6)alkylthio group that comprises a (C1-C6)alkyl group that is linear or branched that is substituted or not by one or more halogen atoms.

In a particular embodiment, the compound of formula (I) is selected in the group consisting of 1-[4-methylthiophenyl]-3-[3,5-dimethyl-4-carboxydimethylmethyloxy phenyl]prop-2-en-1-one (Elafibranor or GFT505), 1-[4-methylthiophenyl]-3-[3,5-dimethyl-4-isopropyloxy carbonyldimethylmethyloxyphenyl]prop-2-en-1-one, 1-[4-methylthiophenyl]-3-[3,5-dimethyl-4-tertbutyloxycarbonyldimethylmethyloxyphenyl]prop-2-en-1-one, 1-[4-trifluoromethylphenyl]-3-[3,5-dimethyl-4-tertbutyloxycarbonyl dimethylmethyloxyphenyl]prop-2-en-1-one, 1-[4-trifluoromethyl phenyl]-3-[3,5-dimethyl-4-carboxydimethylmethyloxyphenyl]prop-2-en-1-one, 1-[4-trifluoromethyl oxyphenyl]-3-[3,5-dimethyl-4-tertbutyloxycarbonyldimethylmethyloxy phenyl]prop-2-en-1-one, 1-[4-trifluoromethyloxyphenyl]-3-[3,5-dimethyl-4-carboxydimethylmethyl oxyphenyl]prop-2-en-1-one, 2-[2,6-dimethyl-4-[3-[4-(methylthio)phenyl]-3-oxo-propyl]phenoxy]-2-methylpropanoic acid, and 2-[2,6-dimethyl-4-[3-[4-(methylthio) phenyl]-3-oxo-propyl]phenoxy]-2-methyl-propanoic acid isopropyl ester.

In a more particular embodiment, the PPAR agonist is 1-[4-methylthiophenyl]-3-[3,5-dimethyl-4-carboxydimethylmethyloxy phenyl]prop-2-en-1-one (or Elafibranor or ELA-GFT505), or a pharmaceutically acceptable salt thereof.

CVC is (S)-8-[4-(2-Butoxyethoxy)phenyl]-1-isobutyl-N-[4-[[(1-propyl-1H-imidazol-5-yl)methyl]sulfinyl]phenyl]-1,2,3,4-tetrahydro-1-benzazocine-5-carboxamide. Details of the composition of matter of cenicriviroc are disclosed in US Patent Application Publication No. 2012/0232028. Details of related formulations are disclosed in U.S. Application No. 61/823,766 which is hereby incorporated by reference in its entirety for all purposes. In one embodiment, CVC is in the form of an acid addition salt. In a particular embodiment, the an addition salt of CVC is included in the combination product, such as CVC mesylate, e.g., (S)-8-[4-(2-Butoxyethoxy)phenyl]-1-isobutyl-N-[4-[[(1-propyl-1H-imidazol-5-yl)methyl]sulfinyl]phenyl]-1,2,3,4-tetrahydro-1-benzazocine-5-carboxamide monomethanesulfonoate. In one embodiment, the CVC mesylate is a crystalline material, such as a pale greenish-yellow crystalline powder. In one embodiment, the CVC mesylate is freely soluble in glacial acetic acid, methanol, benzyl alcohol, dimethylsulfoxide, and N,N-dimethylformamide; soluble in pyridine and acetic anhydride; and sparingly soluble in 99.5% ethanol; slightly soluble in acetonitrile, 1-octanol, and tetrahydrofuran; and practically insoluble in ethyl acetate and diethylether. In one embodiment, the CVC mesylate is freely soluble in aqueous solution from pH 1 to 2; sparingly soluble at pH 3 and practically insoluble from pH 4 to 13 and in water.

In a particular aspect, the invention relates to a combination product comprising:
(i) CVC or a derivative, or an analogue, or a pharmaceutically acceptable salt or solvate thereof,
(ii) a PPAR agonist, in particular a compound of formula (I) or a pharmaceutically acceptable salt thereof, in particular Elafibranor or a pharmaceutically acceptable salt thereof.

In a particular embodiment, the combination product is a composition comprising:
(i) CVC or a derivative, or an analogue, or a pharmaceutically acceptable salt or solvate thereof,
(ii) a PPAR agonist, in particular a compound of formula (I) or a pharmaceutically acceptable salt thereof, in particular Elafibranor or a pharmaceutically acceptable salt thereof; and
(iii) a pharmaceutically acceptable carrier.

In a particular embodiment, the combination product is a kit of parts comprising:
(i) CVC or a derivative, or an analogue, or a pharmaceutically acceptable salt or solvate thereof,
(ii) a PPAR agonist, in particular a compound of formula (II) or a pharmaceutically acceptable salt thereof, in particular Elafibranor or a pharmaceutically acceptable salt thereof;
for sequential, separate or simultaneous use, in particular in the treatment of any of the diseases mentioned herein.

According to an embodiment, the combination product comprises (i) CVC or a pharmaceutically acceptable salt thereof, and (ii) Elafibranor or a pharmaceutically acceptable salt thereof.

The invention further relates to a combination product as defined herein, for use in a method for the treatment of a disease, such as an immune (e.g. autoimmune), inflammatory, metabolic, fibrotic or cholestatic disease.

In a further aspect, the invention relates to the combination product of the invention, for use in the inhibition of proliferation and/or activation of fibroblasts responsible for the production of collagen fibers and/or responsible for the production of the extracellular matrix.

According to the present invention, the term "autoimmune disease" is used to designate a condition that arises from an abnormal immune response of the body against substances and tissues normally present in the body. The disease may be restricted to certain organs (e.g in type I diabetes or autoimmune thyroiditis) or involve a particular tissue in different places (e.g. in Goodpasture's disease, affection of the basement membrane in the lung and the kidney).

The term "inflammation" is used to designate a condition that arise from a protective response involving host cells, blood vessels, and proteins and other mediators which may serve to eliminate the cause of cell/tissue injury, as well as the necrotic cells/tissues resulting from the original insult, and to initiate the process of repair. The inflammatory reaction may be manifested by pain, heat, redness, swelling, blood vessels dilatation, blood flow increase and loss of function.

The terms "fibrosis", "fibrotic disease", "fibrotic disorder" and declinations thereof denote a pathological condition of excessive deposition of fibrous connective tissue in an organ or tissue. More specifically, fibrosis is a pathologic process, which includes a persistent fibrotic scar formation and overproduction of extracellular matrix, by the connective tissue, as a response to tissue damage. Physiologically, the deposit of connective tissue can obliterate the architecture and function of the underlying organ or tissue.

According to the present invention, the fibrosis may be any organ or tissue fibrosis. Illustrative, non-limiting examples of particular organ fibrosis include liver, kidney, skin, epidermis, endodermis, muscle, tendon, cartilage, heart, pancreas, lung, uterus, nervous system, testis, ovary, adrenal gland, artery, vein, colon, intestine (e.g. small intestine), biliary tract, soft tissue (e.g. mediastinum or retroperitoneum), bone marrow, joint and stomach fibrosis.

In a preferred embodiment, the fibrotic disorder is selected in the group consisting of a liver, gut, lung, heart, kidney, muscle, skin, soft tissue (e.g. mediastinum or retroperitoneum), bone marrow, intestinal, and joint (e.g. knee, shoulder or other joints) fibrosis.

In a more preferred embodiment, the fibrotic disorder is selected in the group consisting of the liver, lung, skin, kidney and intestinal fibrosis.

In a more preferred embodiment of the present invention, treated fibrotic disorder is selected in the group consisting of the following non exhaustive list of fibrotic disorders: non-alcoholic steatohepatitis (NASH), pulmonary fibrosis, idiopathic pulmonary fibrosis, skin fibrosis, eye fibrosis, endomyocardial fibrosis, mediastinal fibrosis, myelofibrosis, retroperitoneal fibrosis, progressive massive fibrosis (a complication of coal workers' pneumoconiosis), proliferative fibrosis, neoplastic fibrosis, lung fibrosis consecutive to chronic inflammatory airway disease (COPD, asthma, emphysema, smoker's lung, tuberculosis, IPF), alcohol or drug-induced liver fibrosis, liver cirrhosis, infection-induced liver fibrosis, radiation or chemotherapeutic-induced fibrosis, nephrogenic systemic fibrosis, Crohn's disease, ulcerative colitis, keloid, old myocardial infarction, scleroderma/systemic sclerosis, arthrofibrosis, some forms of adhesive capsulitis, chronic fibrosing cholangiopathies such as Primary Sclerosing Cholangitis (PSC) and (PBC), biliary atresia, familial intrahepatic cholestasis type 3 (PFIC3), peri-implantational fibrosis and asbestosis.

Cholestasis is defined as a decrease in bile flow due to impaired secretion by hepatocytes (hepato-cellular cholestasis) or to obstruction of bile flow through intra- or extra-hepatic bile ducts (obstructive cholestasis). In clinical practice, cholestasis is any condition in which the flow of bile from the liver is slowed or blocked.

Examples of inflammatory diseases, fibrotic diseases, metabolic diseases and cholestatic diseases include metabolic liver diseases, non-alcoholic fatty liver disease (NAFLD), non-alcoholic steatohepatitis (NASH), drug-induced liver diseases, alcohol-induced liver diseases, infectious agent induced liver diseases, inflammatory liver diseases, immune system dysfunction-mediated liver diseases, dyslipidemia, cardiovascular diseases, restenosis, syndrome X, metabolic syndrome, diabetes, obesity, hypertension, chronic cholangiopathies such as Primary Sclerosing Cholangitis (PSC), Primary Biliary Cholangitis (PBC), biliary atresia, familial intrahepatic cholestasis type 3 (PFIC3), inflammatory bowel diseases, Crohn's disease, ulcerative colitis, keloid, old myocardial infarction, scleroderma/systemic sclerosis, inflammatory diseases, neurodegenerative diseases, cancers, liver cancer, hepatocallular carcinoma, gastrointestinal cancer, gastric cancer, meningioma associated with neurofibromatosis, pancreatic neuroendocrine tumors, pancreatic exocrine tumors, leukemia, myeloproliferative/myelodisplastic diseases, mastocytosis, dermatofibrosarcoma, solid tumors including breast, lung, thyroid or colorectal cancer, a prostate cancer, liver fibrosis or cirrhosis of any origin, metabolic disease-induced liver fibrosis or cirrhosis, NAFLD-induced fibrosis or cirrhosis, NASH-induced fibrosis or cirrhosis, alcohol-induced liver fibrosis or cirrhosis, drug-induced liver fibrosis or cirrhosis, infectious agent-induced liver fibrosis or cirrhosis, parasite infection-induced liver fibrosis or cirrhosis, bacterial infection-induced liver fibrosis or cirrhosis, viral infection-induced fibrosis or cirrhosis, HBV-infection induced liver fibrosis or cirrhosis, HCV-infection induced liver fibrosis or cirrhosis, HIV-infection induced liver fibrosis or cirrhosis, dual HCV and HIV-infection induced liver fibrosis or cirrhosis, radiation- or chemotherapy-induced fibrosis or cirrhosis, biliary tract fibrosis, liver fibrosis or cirrhosis due to any chronic cholestatic disease, gut fibrosis of any etiology, Crohn's disease-induced fibrosis, ulcerative colitis-induced fibrosis, intestine (e.g. small intestine) fibrosis, colon fibrosis, stomach fibrosis, skin fibrosis, epidermis fibrosis, endodermis fibrosis, skin fibrosis due to scleroderma/systemic sclerosis, lung fibrosis, lung fibrosis consecutive to chronic inflammatory airway diseases, such as COPD, asthma, emphysema, smoker's lung, tuberculosis, pulmonary fibrosis, idiopathic pulmonary fibrosis (IPF), heart fibrosis, kidney fibrosis, nephrogenic systemic fibrosis, muscle fibrosis, soft tissue (e.g. mediastinum or retroperitoneum) fibrosis, bone marrow fibrosis, joint fibrosis, tendon fibrosis, cartilage fibrosis, pancreas fibrosis, uterus fibrosis, nervous system fibrosis, testis fibrosis, ovary fibrosis, adrenal gland fibrosis, artery fibrosis, vein fibrosis, eye fibrosis, endomyocardial fibrosis, mediastinal fibrosis, myelofibrosis, retroperitoneal fibrosis, progressive massive fibrosis (a complication of coal workers' pneumoconiosis), proliferative fibrosis, neoplastic fibrosis, peri-implantational fibrosis and asbestosis, arthrofibrosis, adhesive capsulitis.

Preferably, the disease is selected in the group consisting of metabolic liver diseases, non-alcoholic fatty liver disease (NAFLD), non-alcoholic steatohepatitis (NASH), drug-induced liver diseases, alcohol-induced liver diseases, infectious agent induced liver diseases, inflammatory liver diseases, immune system dysfunction-mediated liver diseases, dyslipidemia, cardiovascular diseases, restenosis, syndrome X, metabolic syndrome, diabetes, obesity, hypertension, chronic cholangiopathies such as Primary Sclerosing Cholangitis (PSC), Primary Biliary Cholangitis (PBC), biliary atresia, familial intrahepatic cholestasis type 3 (PFIC3), inflammatory bowel diseases, Crohn's disease, ulcerative colitis, liver cancer, hepatocallular carcinoma, gastrointestinal cancer, gastric cancer, colorectal cancer, metabolic disease-induced liver fibrosis or cirrhosis, NAFLD-induced fibrosis or cirrhosis, NASH-induced fibrosis or cirrhosis, alcohol-induced liver fibrosis or cirrhosis, drug-induced liver fibrosis or cirrhosis, infectious agent-induced liver fibrosis or cirrhosis, parasite infection-induced liver fibrosis or cirrhosis, bacterial infection-induced liver fibrosis or cirrhosis, viral infection-induced fibrosis or cirrhosis, HBV-infection induced liver fibrosis or cirrhosis, HCV-infection induced liver fibrosis or cirrhosis, HIV-infection induced liver fibrosis or cirrhosis, dual HCV and HIV-infection induced liver fibrosis or cirrhosis, radiation- or chemotherapy-induced fibrosis or cirrhosis, biliary tract fibrosis, liver fibrosis or cirrhosis due to any chronic cholestatic disease, gut fibrosis of any etiology, Crohn's disease-induced fibrosis, ulcerative colitis-induced fibrosis, intestine (e.g. small intestine) fibrosis, colon fibrosis, stomach fibrosis, lung fibrosis, lung fibrosis consecutive to chronic inflammatory airway diseases, such as COPD, asthma, emphysema, smoker's lung, tuberculosis, pulmonary fibrosis, idiopathic pulmonary fibrosis (IPF).

Therefore, according to the invention, the treatment of a immune (e.g. autoimmune), inflammatory, metabolic, fibrotic or cholestatic disease involves the administration of the combination product of the present invention, for example in the form of a pharmaceutical composition or of a kit of parts containing components (i) and (ii) of the combination, to a subject having a declared disorder to cure, delay, reverse or slow down the progression of the disorder, thus improving the condition of the patient or to a healthy subject, in particular a subject who is at risk of developing such disease.

The subject to be treated is a mammal, preferably a human. The subject to be treated according to the invention can be selected on the basis of several criteria associated to fibrotic diseases such as previous drug treatments, associated pathologies, genotype, exposure to risk factors, viral infection, as well as on the basis of the detection of any relevant biomarker that can be evaluated by means of imaging methods and immunological, biochemical, enzymatic, chemical, or nucleic acid detection methods.

In a particular embodiment, the combination product is a kit of parts comprising:
  (i) CVC compound or a derivative, an analogue, a salt or solvate thereof,
  (ii) a PPAR agonist, in particular a compound of formula (I) or a pharmaceutically acceptable salt thereof, in particular Elafibranor or a pharmaceutically acceptable salt thereof;
for sequential, separate or simultaneous use in the treatment of any of the diseases mentioned above.

The PPAR agonist of formula (I) may be in the form of a pharmaceutically acceptable salt, hydrate, solvate, polymorph, or a co-crystal.

The PPAR agonist of formula (I) may also be in the form of a hydrate, solvate, polymorph, or a co-crystal of a salt.

According to the invention the combinations comprising (i) at least CVC or a derivative, analogue, salt or solvate thereof, (ii) at least a PPAR agonist of formula (I), and (iii) optionally one or more pharmaceutically acceptable carriers is selected so that the combination of the invention provides a synergistic action against immune (e.g. autoimmune), inflammatory, metabolic, fibrotic or cholestatic disease, in particular a inflammatory, metabolic, fibrotic or cholestatic disease. Such synergy may be determined according to methods well-known in the art, such as by using the Excess Over Bliss (EOB) method described in the examples. The present invention thus relates to a combination product comprising CVC or a pharmaceutically acceptable salt thereof, and of Elafibranor or of a pharmaceutically acceptable salt thereof, each in a synergistic amount so that they may elicit a therapeutic effect better than the therapeutic effect obtained with each of these compounds administered alone.

The invention provides also a method of treatment of an immune (e.g. autoimmune), inflammatory, metabolic, fibrotic or cholestatic disease.

The subject to be treated according to the invention can be selected on the basis of several criteria associated to immune (e.g. autoimmune), inflammatory, metabolic, fibrotic and cholestatic diseases such as previous drug treatments, associated pathologies, genotype, exposure to risk factors, viral infection, as well as any other relevant biomarker that can be evaluated by means of imaging methods and immunological, biochemical, enzymatic, chemical, or nucleic acid detection method.

In another embodiment, the combination of the invention is for simultaneous, sequential or separate administration in therapy, therefore being possibly included in different compositions. In case of sequential administration, CVC or a derivative, analogue, salt or solvate thereof may be administrated prior to the PPAR agonist of formula (I), and preferentially Elafibranor, or the PPAR agonist of formula (I), and preferentially Elafibranor is administered prior to CVC or its derivatives, or an analogue, or a salt or solvate thereof.

Combination of CVC or a derivative, analogue, salt or solvate thereof; and a PPAR agonist of formula (I), in particular Elafibranor, can be formulated as pharmaceutically acceptable non-toxic salts obtained from organic or inorganic bases or acids of CVC, a derivative, analogue, salt or solvate thereof, or of a PPAR agonist of formula (I), if particular of Elafibranor. These salts can be obtained during the final purification step of the compound or by incorporating the salt into the previously purified compound.

The pharmaceutical compositions of the present invention comprising (i) CVC or a derivative, salt or solvate thereof; and (ii) a PPAR agonist of formula (I), in particular Elafibranor, can also comprise one or several excipients or vehicles, acceptable within a pharmaceutical context (e.g. saline solutions, physiological solutions, isotonic solutions, etc., compatible with pharmaceutical usage and well-known by one of ordinary skill in the art).

These compositions can also comprise one or several agents or vehicles chosen among dispersants, solubilisers, stabilisers, preservatives, etc. Agents or vehicles useful for these formulations (liquid and/or injectable and/or solid) are particularly methylcellulose, hydroxymethylcellulose, carboxymethylcellulose, polysorbate 80, mannitol, gelatin, lactose, vegetable oils, acacia, liposomes, etc.

These compositions can be formulated in the form of injectable suspensions, gels, oils, ointments, pills, suppositories, powders, gel caps, capsules, aerosols, etc., eventually by means of galenic forms or devices assuring a prolonged and/or slow release. For this kind of formulation, agents such as cellulose, carbonates or starches can be advantageously used.

The pharmaceutical compositions of the present invention comprising CVC or a derivative, analogue, salt or solvate thereof; and (ii) a PPAR agonist of formula (I), in particular Elafibranor, may be administered by different routes and in different forms.

For example, the compound(s) may be administered via a systemic way, per os, parenterally, by inhalation, by nasal spray, by nasal instillation, or by injection, such as for example intravenously, by intra-muscular route, by subcutaneous route, by transdermal route, by topical route, by intra-arterial route, etc.

Of course, the route of administration will be adapted to the form of CVC or its derivative, analogue, salt or solvate thereof in combination with one or more PPAR agonist of formula (I), in particular with Elafibranor, according to procedures well known by those skilled in the art.

CVC or a derivative, analogue, salt or solvate thereof in combination with a PPAR agonist of formula (I), in particular with Elafibranor, is administered in a therapeutically effective amount.

The frequency and/or dose relative to the administration can be adapted by one of ordinary skill in the art, in function of the patient, the pathology, the form of administration, etc.

Typically, the combination (such as in the form of a pharmaceutical composition or a kit-of-parts) of the present invention can be administered for the treatment of a fibrotic disease at a dose for compound of Formula (I) comprised between 10 mg/day to 2000 mg/day, such as from 50 mg/day to 1000 mg/day, and particularly from 70 mg/day to 200 mg/day.

The dose of the CVC or derivative, analogue, salt, solvate, ester and/or prodrug thereof is comprised between 10 mg/day to about 1000 mg/day, such as a dose from about 30 mg/day to about 500 mg/day. In a particular embodiment, CVC is administered at a dose comprised between 100 mg/day to 250 mg/day. In a further particular embodiment, CVC is administered at a dose of 150 mg/day. In a further particular embodiment, 150 mg of CVC is administered orally once daily, optionally taken every morning with food.

In a particular embodiment of the invention, Elafibranor is administered, at a dose comprised between 10 mg/day to 2000 mg/day. In a further particular embodiment, Elafibranor is administered at a dose comprised between 70 mg/day and 200 mg/day, such as between 80 and 120 mg/day. In another embodiment, Elafibranor is administered at a dose of 80 or 120 mg/day. In a further particular embodiment, 80 or 120 mg of Elafibranor is taken in the form of two tablets containing Elafibranor per day orally before breakfast with a glass of water each morning.

In a preferred embodiment of the invention, CVC is used in combination with Elafibranor at a dose comprised between 100 mg/day to 250 mg/day for CVC (e.g. 150 mg/day) and 80 to 120 mg/day for Elafibranor (e.g. 80 or 120 mg/day).

In another preferred embodiment, the active ingredients are administered as one or more pharmaceutical composition(s) in the form of a pill intended for an oral ingestion.

Administration can be performed daily or even several times per day, if necessary.

In a particular embodiment, the invention relates to a combination of the present invention, further combined to at least one other therapeutically active agent, such as other molecules with known anti-inflammatory, antimetabolic, antifibrotic or anticlolestatic activity. This further combination of the present invention is useful for the treatment of an inflammatory diseases, metabolic, fibrotic and cholestatic disease.

According to a variant of this embodiment, the combination product of the invention can be combined with any antifibrotic compound such as pirfenidone or receptor tyrosine kinase inhibitors (RTKIs) such as Nintedanib, sorafenib and other RTKIs, or angiotensin II (AT1) receptor blockers, or CTGF inhibitor, or any antifibrotic compound susceptible to interfere with the TGFβ- and BMP-activated pathways including activators of the latent TGFβ complex such as MMP2, MMP9, THBS1 or cell-surface integrins, TGFβ receptors type I (TGFBRI) or type II (TGFBRII) and their ligands such as TGFβ, Activin, inhibin, Nodal, anti-MOllerian hormone, GDFs or BMPs, auxiliary co-receptors (also known as type III receptors), or components of the SMAD-dependent canonical pathway including regulatory or inhibitory SMAD proteins, or members of the SMAD-independent or non-canonical pathways including various branches of MAPK signaling, TAK1, Rho-like GTPase signaling pathways, phosphatidylinositol-3 kinase/AKT pathways, TGFβ-induced EMT process or canonical and non-canonical Hedgehog signaling pathways including Hh ligands or target genes, or any members of the WNT, or Notch pathways which are susceptible to influence TGFβ signaling.

Thus, the invention also relates to a pharmaceutical composition, in particular for its use in a method for the treatment of a fibrotic disease, comprising (i) CVC or a derivative, analogue, salt or solvate thereof, and (ii) one or more PPAR agonist of formula (I), in combination with at least one therapeutically active agent with known antifibrotic activity selected from pirfenidone or receptor tyrosine kinase inhibitors (RTKIs) such as Nintedanib, sorafenib and other RTKIs, or angiotensin II (AT1) receptor blockers, or CTGF inhibitor, or antifibrotic compound susceptible to interfere with the TGFβ- and BMP-activated pathways including activators of the latent TGFβ complex such as MMP2, MMP9, THBS1 or cell-surface integrins, TGFβ receptors type I (TGFBRI) or type II (TGFBRII) and their ligands such as TGFβ, Activin, inhibin, Nodal, anti-Müllerian hormone, GDFs or BMPs, auxiliary co-receptors (also known as type III receptors), or components of the SMAD-dependent canonical pathway including regulatory or inhibitory SMAD proteins, or members of the SMAD-independent or non-canonical pathways including various branches of MAPK signaling, TAK1, Rho-like GTPase signaling pathways, phosphatidylinositol-3 kinase/AKT pathways, TGFβ-induced EMT process, or canonical and non-canonical Hedgehog signaling pathways including Hh ligands or target genes, or any members of the WNT, or Notch pathways which are susceptible to influence TGFβ signaling, for use in a method for treating a fibrotic disorder.

In another particular embodiment, other classes of molecules that could also be combined with CVC or a derivative, analogue, salt or solvate thereof, and with one or more PPAR agonist of formula (I), include JAK/STAT inhibitors, or other anti-inflammatory and/or immunosuppressant agents. The non exhaustive list of these agents includes but is not limited to glucocorticoids, NSAIDS, cyclophosphamide, nitrosoureas, folic acid analogs, purine analogs, pyrimidine analogs, methotrexate, azathioprine, mercaptopurine, ciclosporin, myriocin, tacrolimus, sirolimus, mycophenolic acid derivatives, fingolimod and other sphingosine-1-phosphate receptor modulators, monoclonal and/or polyclonal antibodies against such targets as proinflammatory cytokines and proinflammatory cytokine receptors, T-cell receptor, integrins.

Other classes of molecules that could also be combined with the combination product of the invention include molecules that could potentially enhance the exposure or the effect of CVC or a derivative, analogue, salt or solvate thereof, and of the one or more PPAR agonist of formula (I).

In another embodiment, CVC or a derivative, analogue, salt or solvate thereof, and the one or more PPAR agonist of formula (I), is administered as the sole active ingredients.

Accordingly, the invention also relates to a pharmaceutical composition for use in a method for the treatment of an immune (e.g. autoimmune), inflammatory, metabolic, fibrotic or cholestatic disease comprising (i) a compound selected from CVC or a derivatives, analogue, salt or solvate thereof, and (ii) one or more PPAR agonist of formula (I), wherein said (i) and (ii) are the only active ingredients in the composition.

In a further embodiment, the present invention provides methods of treating an immune (e.g. autoimmune), inflammatory diseases, metabolic, fibrotic or cholestatic disease comprising the administration of the combination of the present invention, in particular in the form of a pharmaceutical composition or of a kit-of-parts containing CVC or a derivative, or analogue, salt or solvate thereof, and one or more PPAR agonist of formula (I).

The invention is further described with reference to the following, non-limiting, examples.

Examples

Materials and Methods

Evaluation of Elafibranor, CVC and their Combination in a Vitro Model of Hepatic Fibrogenesis Compounds were dissolved in dimethyl sulfoxide (DMSO, Fluka cat #41640). CVC was obtained commercially from CLINISCIENCES (Ref: A13643-10, Batch number: 497223-25-3). Bezafibrate was synthesized at Genfit.

hHSC Culture

The human primary hepatic stellate cells (hHSC; Innoprot) were cultured in STeCM medium (ScienCell cat #5301) that was supplemented with 2% fetal bovine serum (FBS, ScienCell cat #0010), 1% penicillin/streptomycin (ScienCell cat #0503) and stellate cell growth supplement (SteCGS; ScienCell cat #5352). Cell-culture flasks were coated with Poly-L Lysine (Sigma cat #P4707) for a better adherence.

Preparation of Compositions: 2 Components Combination Matrix (CVC/PPAR Agonist)

2 Components Combination Matrix (CVC/Elafibranor)

Cenicriviroc (CVC) was obtained commercially from CLINISCIENCES (Ref: A13643-10, CAS number: 497223-25-3). Bezafibrate and Elafibranor (GFT505) were synthesized at Genfit.

For these experiments, a checkerboard matrix was generated. CVC and Elafibranor stocks were serially diluted in DMSO in a 5-points series in a row (Elafibranor) and a 6_points series in a column (Cenicriviroc) of a 96-well plate. Subsequently, the 6×7 combination matrix was generated by 1:1 mixing of all single agent concentrations. The test concentrations for each compound were chosen based on the respective $IC_{50}$ of each compound as single agent obtained by measuring α-SMA content in the HSC model stimulated with TGF-β1.

2 Components Combination Matrix (CVC/Bezafibrate)

Bezafibrate was dissolved in dimethyl sulfoxide (DMSO, Fluka cat #41640) and serially diluted in a 5-points series in a row (Bezafibrate) and a 6_points series in a column (CVC) of a 96-well plate. Subsequently, the 6×7 combination matrix was generated by 1:1 mixing of all single agent concentrations. The test concentrations for each compound were chosen based on the respective $IC_{50}$ of each compound as single agent obtained by measuring of each compound as single agent obtained by measuring α-SMA content in the HSC model stimulated with TGF-β1.

Activation of hHSC with TGF-11 and Compound Treatment

The human primary hepatic stellate cells (hHSC; Innoprot) were cultured under standard conditions, as described above. The cells were subsequently plated at a density of $2 \times 10^4$ cells/well into 96-well plates for the measure of α-SMA by ELISA.

The next day, cell-culture medium was removed, and cells were washed with PBS (Invitrogen cat #14190). hHSC were deprived for 24 hours in serum-free and SteCGS-free medium. For the treatments with CVC, Elafibranor, Bezafibrate and the pairwise combinations of CVC/Elafibranor and CVC/Bezafibrate, the serum-deprived hHSC were pre-incubated for 1 hour with the compounds followed by addition of the profibrogenic stimuli TGF-β1 (PeproTech cat #100-21, 1 ng/mL) in serum-free and SteCGS-free medium for an additional 48 hour period.

α-SMA ELISA

The level of α-SMA was measured using a Sandwich ELISA. Briefly, the wells of an ELISA plate were first coated with the capture antibody (mouse monoclonal anti-ACTA2, Abnova) at 4° C. overnight. After 3 washes in PBS+0.2% Tween 20, a blocking solution consisting of PBS+0.2% BSA was added for one hour followed by another washing cycle. The cell lysates were transferred into the wells for binding to the capture antibody for a period of 2 h at room temperature. After the washing procedure, the detection antibody (biotinylated mouse monoclonal anti-ACTA2, Abnova) was added for 2 hours at room temperature followed by 3 washes. For the detection, an HRP-conjugated Streptavidin (R&D Systems cat #DY998) was first applied for 30 min at room temperature. After washing, the HRP substrate TMB (BD, cat #555214) was added and incubated for 7 min at room temperature in the dark. Upon oxidation, TMB forms a water-soluble blue reaction product that becomes yellow with addition of sulfuric acid (solution stop), enabling accurate measurement of the intensity at 450 nm using a spectrophotometer. The developed color is directly proportional to the amount of α-SMA present in the lysate.

Determination of Synergism by Excess Over Bliss (EOB) Method

The values obtained in the α-SMA ELISA assays were first transformed into percentage inhibitions over TGF-β1 control. Inhibition above 20% was considered as biologically relevant. Then, using these percentage inhibitions, EOB (Excess Over Bliss) was determined to define the synergistic effects of drug combinations. Expected Bliss additivism score (E) was firstly determined by the equation: $E = (A+B) - (A \times B)$ where A and B are the percentage inhibition of Elafibranor (A) (or Bezafibrate) and Cenicriviroc (CVC) (B) at a given dose. The difference between the Bliss expectation and the observed inhibition of the combined CVC/Elafibranor (or Bezafibrate) at the same dose is the 'Excess over Bliss' score.

Excess over Bliss score=0 indicates that the combination treatment is additive (as expected for independent pathway effects);

Excess over Bliss score>0 indicates activity greater than additive (synergy); and Excess over Bliss score<0 indicates the combination is less than additive (antagonism).

For the combinations Elafibranor+CVC and Bezafibrate+CVC, an additional total Bliss score was calculated by summation of all EOB.

To validate the synergism, the experimental values corresponding to top EOB score for CVC/Elafibranor combination were plotted in a bar graph.

The significance of the observed differences between CVC/Elafibranor or CVC/Bezafibrate over the highest single agent was determined by a student's t-test with * $p<0.05$;  $p<0.01$; * $p<0.001$ Evaluation of Elafibranor, CVC and their Combination in a Chronic CDFF Diet Model (8 Weeks)

The preventive effects of Elafibranor alone, CVC alone and their combination were assessed in a fibrosing NASH model of mice fed a CDAA+2% cholesterol+30% Milk fat diet and High Fructose Corn Syrup 55 (55% fructose/45% glucose for a final concentration of 42 g/L) in drinking water (Mells et al J Nutr Biochem 2015). 5-6 weeks old male C57Bl/6J mice were fed a control (CSAA) diet (n=4), CDFF diet (n=12), or CDFF diet supplemented with Elafibranor 3 mg/kg/day, CVC 10 mg/kg/day or combined drugs (Elafibranor 3 mg/kg/day combined to CVC 10 mg/kg/day) (n=8 per group) for 8 weeks.

The body weight, the food and water intake were monitored twice per week. On the last day of treatment, plasma samples were obtained from retro-orbital blood sampling and mice were sacrificed after a 6 h-fasting period. The liver was rapidly excised for biochemical and histological analyses. All animal procedures were performed according to standard protocols and in accordance with the standard recommendations for the proper care and use of laboratory animals.

Histology

Tissue Embedding and Sectioning

The liver slices were fixed in a formalin 4% solution. Then, the liver pieces were washed 30 minutes in PBS, and dehydrated in ethanol solutions (successive baths at 70, 80, 95 and 100% ethanol). The liver pieces were incubated in three different baths of Xylene (Honeywell cat #534056), followed by two baths in liquid paraffin (59° C.). Liver pieces were then put into racks that were gently filled with Histowax® to completely cover the tissue.

The paraffin blocks containing the tissue pieces were removed from the racks and stored at room temperature. The liver blocks were cut into 3 µm slices.

Hematoxylin/Eosin/Safranin Staining

Liver sections were deparaffinized, rehydrated and incubated for 3 minutes in Mayer's Hematoxylin (Microm, cat #F/C0303). Then, the liver sections were rinsed in water and incubated 1 minute in a Eosin Y 0.5% alcoholic (VWR, cat #1.02439.0500) and Erythrosin 0.5% solution (VWR, cat #1.15936.0010), and rinsed in with ethanol. Sections were then incubated for 2 minutes in Safranin, and were eventually dehydrated and mounted using the CV Mount medium (Leica, cat #046430011).

Histological Examinations

A technician blinded to the source of each liver specimen performed histological examinations. Virtual slides were generated using the Pannoramic 250 scanner from 3D Histech. For each animal, a score summarizing the main histological lesions of NASH was attributed according to the NASH Clinical Research Network (Kleiner 2005, Brunt 1999). Briefly, steatosis, lobular inflammation and hepatocyte ballooning were scored. The NAFLD Activity Score (NAS score) was established for each individual as the unweighted sum of the steatosis (0-3), lobular inflammation (0-3) and the ballooning (0-2) injury grading.

Plasma Liver Enzymes and CK18 Measurement

Alanine aminotransferase (ALT) and aspartate aminotransferase (AST) concentrations were measured in plasma using the Randox kit for Daytona automate (Randox cat #AL 3801 and AS 3804, respectively). Plasma cytokeratin 18-M30, a surrogate marker of apoptosis, was measured using the Mouse Cytokeratin 18-M30 ELISA Kit (CUSABIO cat #CSB-E14265m), according to the manufacturer's recommendations.

Hepatic Gene Expression Analysis

Total RNA was isolated from mouse livers using RNeasy Mini Kit (Qiagen) following manufacturer's instructions. Total RNA were reverse transcribed into cDNA using M-MLV RT (Moloney Murine Leukemia Virus Reverse Transcriptase) (Invitrogen cat #28025) in 1×RT buffer (Invitrogen), 0.5 mM DTT (Invitrogen), 0.18 mM dNTPs (Promega), 200 ng pdN6 (Amersham) and 30 U of RNase inhibitor (Promega).

Quantitative PCR was then carried out using the CFX96 Touch™ Real-Time PCR Detection System (Biorad). Briefly, the PCR reactions were performed in 96-WP format in 25 µl of total volume containing 1 µL of reverse transcription reaction, 0.5 µL of reverse and forward primers (10 pmol each), and 12.5 µl of 2× iQ SYBR Green Supermix (BioRad), using the following primer sequences:

| Gene | Forward | Reverse |
|---|---|---|
| GAPDH | TATGACTCCACTCACGGCAATC (SEQ ID NO: 1) | CACGACATACTCAGCACC (SEQ ID NO: 2) |
| α-SMA (ACTA2) | CTGACAGAGGCACCACTGAACATC (SEQ ID NO: 3) | TCCAGAGTCCAGCACA (SEQ ID NO: 4) |
| Col1α1 | AGGCGAACAAGGTGACAGAGGCC (SEQ ID NO: 5) | AGGAGAACCAGCAGAG (SEQ ID NO: 6) |
| Col1α2 | ATTGGAAGCCGAGGTCCCAGTTT (SEQ ID NO: 7) | GCCCCCAGGTATGCCAG (SEQ ID NO: 8) |
| TGFβ1 | TTGCTTCAGCTCCACAGAGATGGT (SEQ ID NO: 9) | TGTAGAGGGCAAGGAC (SEQ ID NO: 10) |
| TIMP1 | ATTCAAGGCTGTGGGAAATGCTC (SEQ ID NO: 11) | AGAGTACGCCAGGGAAC (SEQ ID NO: 12) |
| MMP2 | TCCCTAAGCTCATCGCAGACGCTT (SEQ ID NO: 13) | CCAAACTTCACGCTCT (SEQ ID NO: 14) |
| TNFα | CGTGGAACTGGCAGAAGAGGAGAC (SEQ ID NO: 15) | AGAAGAGCGTGGTGGC (SEQ ID NO: 16) |
| MCP1 | GCCTGCTGTTCACAGTTGCCCTTT (SEQ ID NO: 17) | GGGACACCTGCTGCTG (SEQ ID NO: 18) |

Expression levels were normalized using the expression of GAPDH gene as a housekeeping gene of reference in samples. For each gene, the standard curves were drawn by selecting the best points (at least three points) in order to have PCR reaction efficiency close to 100% and a correlation coefficient close to 1. Expression levels were determined using the standard curve equation for both the housekeeping gene and the target gene (taking into account the specific PCR efficiency of each target gene).

Results and Conclusions:

Evaluation of Elafibranor, CVC and their Combination in a Vitro Model of Hepatic Fibrogenesis The abnormal persistence of differentiated myofibroblasts is a characteristic of many fibrotic diseases.

Following liver injury, quiescent HSCs undergo a process of activation that is characterized by a differentiation into (α-SMA)-positive myofibroblasts.

Figure 1:
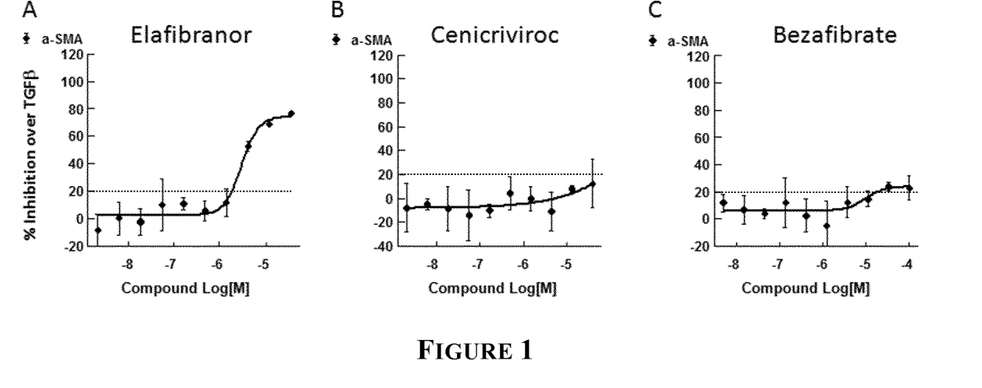
FIG. 1: Differential Antifibrotic Effect of Elafibranor Versus Cenicriviroc, and Bezafibrate in TGFβ-Induced hHSC Serum-deprived HSC were preincubated for 1 hour with Elafibranor (A), Cenicriviroc (B), or Bezafibrate (PPAR pan α/γ/δ) before the activation with the profibrogenic cytokine TGFβ1 (1 ng/ml).
Figure 2:
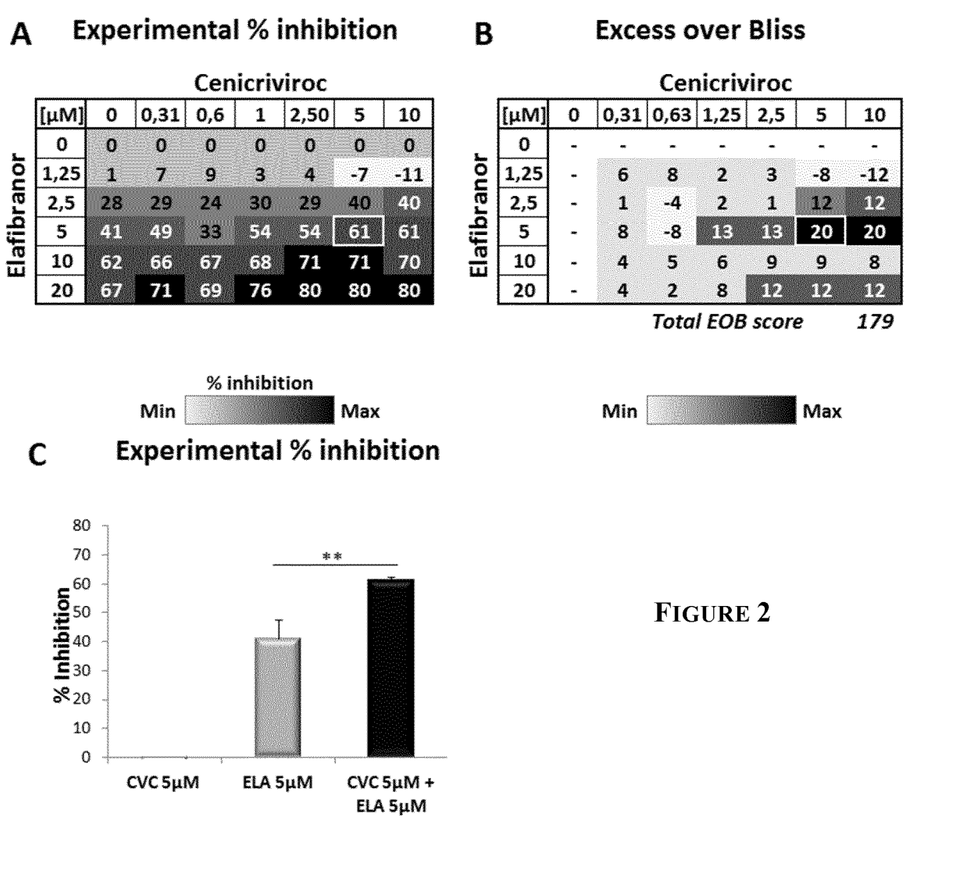
FIG. 2: Combination of Elafibranor with Cenicriviroc Synergistically Inhibits α-SMA in TGFβ1-Induced hHSC Combinations were tested in a dose-response matrix format and analyzed according to the excess over Bliss (EOB) additivism model. Dilution series of Elafibranor (row) and Cenicriviroc (column) were prepared, including their respective DMSO controls. The resulting mixes were added to serum-deprived HSC, 1 hour prior to the activation with the profibrogenic cytokine TGFβ1 (1 ng/ml).
Figure 3:
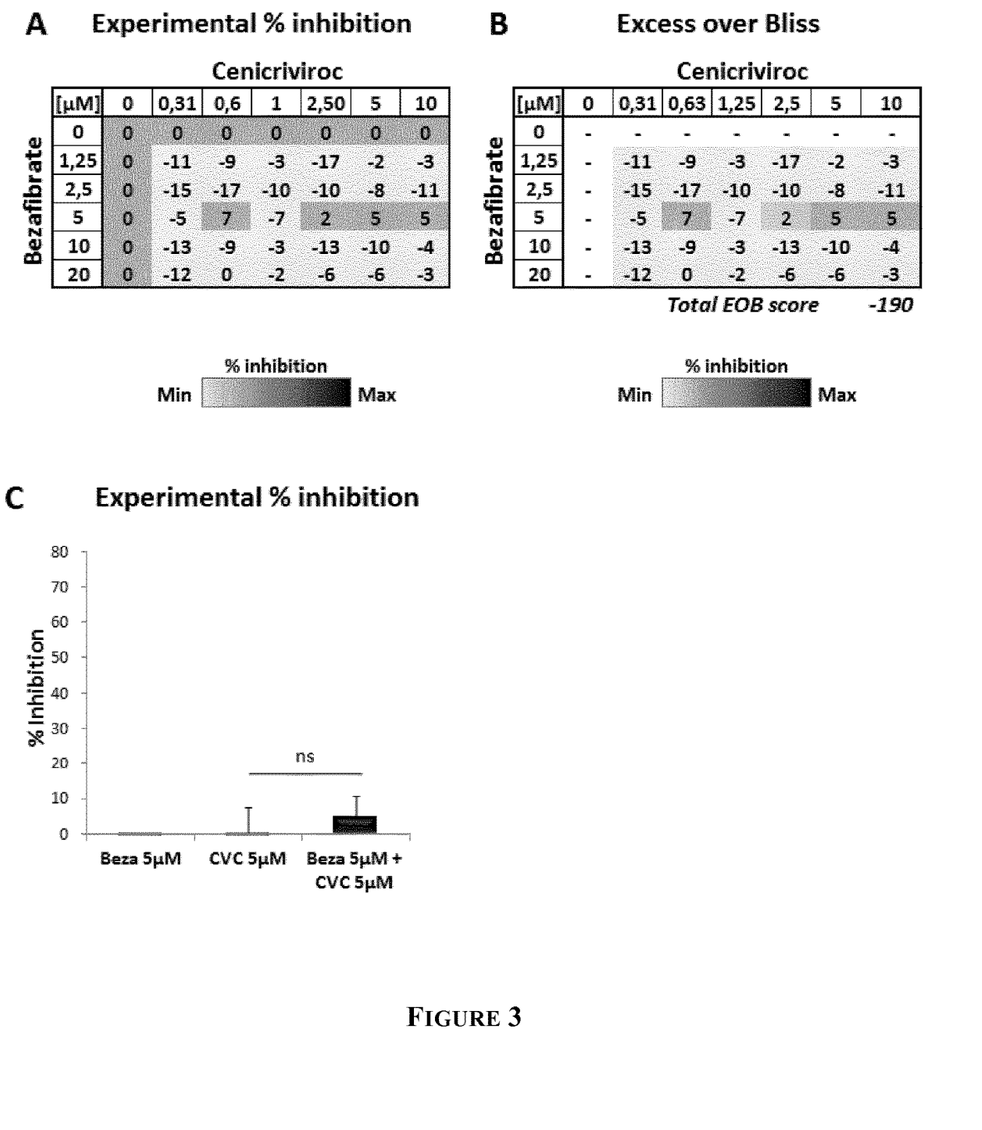
FIG. 3: Bezafibrate does not Synergize with Elafibranor to Reduce Fibrosis in TGFβ1-Induced hHSC Combinations were tested in a dose-response matrix format and analyzed according to the excess over Bliss additivity model. Dilution series of Bezafibrate (row) and Cenicriviroc (column) were prepared, including their respective DMSO controls. The resulting mixes were added to serum-deprived HSC, 1 hour prior to the activation with the profibrogenic cytokine TGFβ1 (1 ng/ml). (A) Percentage inhibition of α-SMA over the TGFβ1 control. (B) Excess over Bliss (EOB) scores were calculated as described in Materials and Methods. Any compound pair with EOB values>10 was considered synergistic (colored from light grey to black). The total EOB score including all combinations was also calculated. (C) Data values derived from the most efficient combination pair were plotted in a bar graph representation. Data are presented as mean (quadruplicates) ±standard deviation (SD). ns, non significant Student's t-test comparing the combination group over the highest single agent.

The PPAR agonist Elafibranor reveals an antifibrotic activity in hHSC activated with the profibrogenic cytokine TGFβ1. The α-SMA marker was reduced by 80% with an $IC_{50}$ of 3.17 µM (FIG. 1A). However, other PPAR agonists like Bezafibrate showed a weak antifibrotic profile (FIG. 1C), suggesting that PPAR agonists are not equivalent regarding their antifibrotic properties. CVC alone did not show a significant effect at all doses in TGFβ-activated HSC (FIG. 1B). In order to evaluate whether the combination of Elafibranor with CVC could reduce fibrosis in a synergistic manner, combination matrix experiments were performed in TGFβ-induced hHSCs. Briefly, CVC and Elafibranor solutions were serially diluted in a checkerboard format generating a 42 combinations matrix covering a large panel of Elafibranor/CVC ratios. Synergy was first determined by calculating Excess Over Bliss scores. These experiments revealed that Elafibranor could synergize with CVC to reduce α-SMA production in activated hHSCs (FIGS. 2A and 2B). One of the best example of synergy is shown in FIG. 2C with 5 µM of each compound. Although 5 µM of CVC alone does not show any antifibrotic activity, its addition to 5 µM of Elafibranor could significantly increase in a synergistic manner the activity of Elafibranor and reached up to 60% of inhibition (in comparison to 40% with 5 µM of Elafibranor). By contrast, the combination of CVC with Bezafibrate revealed much lower EOB scores (FIGS. 3A and 3B) and none of the combinations gave statistically significant results (FIG. 3C).

In conclusion, the applicant has discovered unexpected antifibrotic activities for a combination of a compound of Formula (I) with specific PPAR agonist(s). These results suggest that a combination of a compound of Formula (I) with a PPAR agonist can be synergistic and can provide therapeutic benefits in multiple types of fibrotic diseases.

Evaluation of Elafibranor, CVC and their Combination in a Chronic CDFF Diet Model (8 Weeks)

Western life style is invariably linked with high incidence rate of non-alcoholic steatohepatitis (NASH), a chronic liver disease that often progresses to liver fibrosis and cirrhosis and may ultimately lead to hepatocellular carcinoma. Currently, there is no approved therapy for NASH. Drug combinations directed simultaneously at multiple therapeutic targets have the potential to dramatically improve the drug response and to benefit the widest patient population. Drug combinations were previously tested in other systemic diseases, such as hypertension, dyslipidemia or type 2 diabetes and showed better control of the underlying diseases and decreased the morbidity and the mortality. In recent phase 2B studies, both Elafibranor (PPARα/δ agonist) and CVC have shown efficacy on NASH-induced fibrosis. We wanted to compare their action on relevant NASH pathology outcomes, and to look for therapeutic benefits of the combination.

To achieve this aim, NASH was induced by feeding C57Bl/6J mice with a choline-deficient L-amino-acid-defined-diet supplemented with 2% cholesterol and 30% milk fat, and high fructose corn syrup in drinking water (CDFF diet). Animals in the intervention groups received either Elafibranor (3 mg/kg/day) or CVC (10 mg/kg/day) or both compounds for the entire study period. NASH development was evaluated by histology, liver function tests, and biochemical and molecular analyses.

Figure 4:
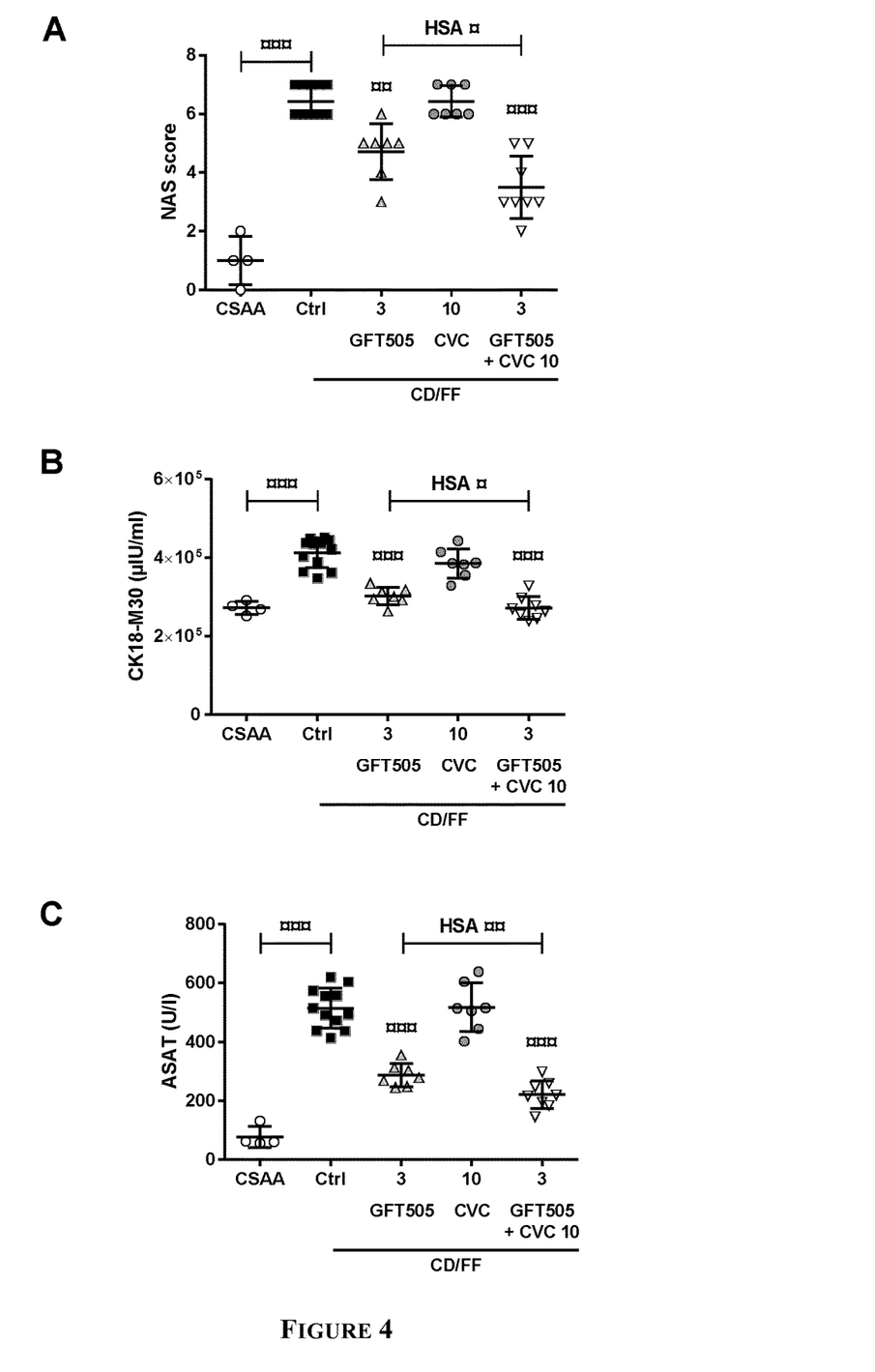
FIG. 4: Effect of Elafibranor (GFT505 3 mg/kg/Day), CVC (10 mg/kg/Day) and their Combination on NASH-Related Parameters in CDFF-Fed Mice.
Figure 5:
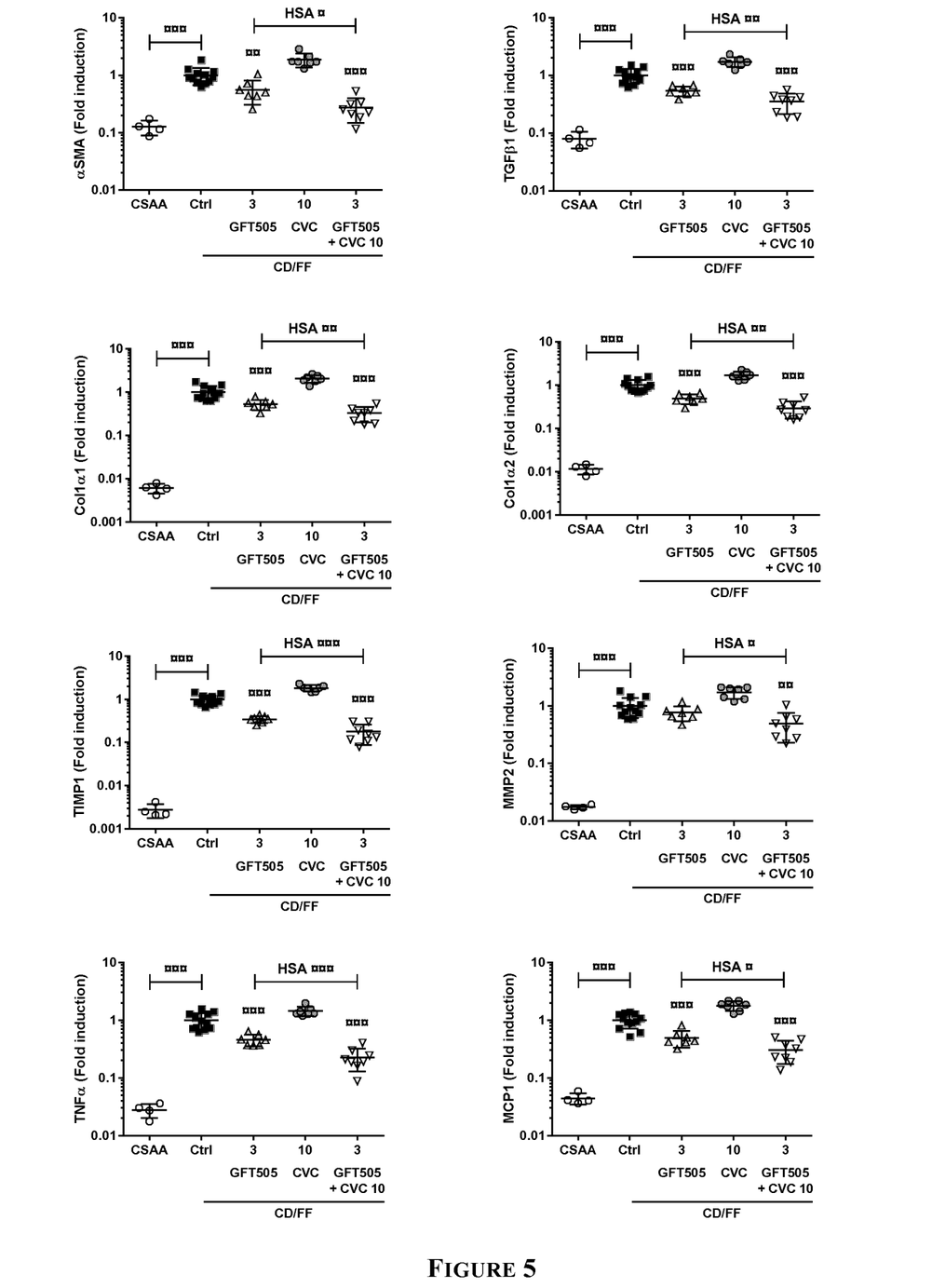
FIG. 5: Effect of Elafibranor (GFT505 3 mg/kg/Day), CVC (10 mg/kg/Day) and their Combination on Expression of Genes Involved in Fibrosis, Tissue Remodeling and Inflammation in CDFF-Fed Mice.

CDFF-fed mice developed NASH with high penetration of severe disease. Advanced steatosis and lobular inflammation were present in all animals resulting in a high NAS score of 6 or 7 (FIG. 4A). Although ballooning was not patent in this model, hepatocellular damages were confirmed with high plasma AST and CK18 levels (FIG. 4B-C). The expression of genes related to fibrogenesis, tissue remodeling and inflammation was increased and consistent with gene signatures that were previously reported in NASH patients with severe disease (FIG. 5).

Elafibranor improved NASH histology by reducing steatosis and hepatic lobular inflammation resulting in a global reduction of the NAS score (FIG. 4A). Elafibranor also reduced liver injury as shown by decreased plasma AST and CK18 concentrations (FIG. 4B-C). Also, Elafibranor decreased the expression of genes related to inflammation, tissue remodeling and fibrogenesis (FIG. 5). Although CVC alone had no effect on these parameters, Elafibranor+CVC combination treatment resulted in a synergistic beneficial effect on disease activity (NAS) and hepatocellular damages (reduction of plasma AST and CK18) (FIG. 4), as well as on the expression of the genes related to inflammation, tissue remodeling and fibrogenesis (FIG. 5).

To conclude, the applicant has shown here a synergistic effect of Elafibranor combined with CVC on NASH parameters and fibrogenesis in the CDFF mouse model. From this study, one can translate that Elafibranor/CVC combination would benefit a wider patient population.

REFERENCES

Brunt E M et al, 1999, Am J Gastroenterol; 94(9):2467-74
Dowman J. K et al., 2010, Q J Med; 103: 71-83
Kleiner D E et al, 2005, Hepatology; 41(6):1313-21
Marchesini G et al. 2003. Hepatology; 37:917-923.
Mells J E et al., 2015. J Nutr Biochem; 26:285-292
Nelson A et al., 2009. J Clin Gastroenterol; 43: 990-994
Neuschwander-Tetri et al., 2003. Hepatology; 38: 1008-1017.
Yeh M et al., 2007. Am J Clin Pathol; 128:837-847.
Shiri-Sverdlov R et al., 2006. J Hepatol; 44: 732-41.
Vuppalanchi R and Chalasani N, 2009. Hepatology; 49: 306-317.

The invention claimed is:

1. A method for treating a cholestatic disease, wherein said method comprises administering to a subject in need thereof a therapeutically effective amount of a combination of:
   (i) cenicriviroc or a pharmaceutically acceptable salt thereof; and
   (ii) elafibranor or a pharmaceutically acceptable salt thereof.

2. The method according to claim 1, wherein the disease is selected in the group consisting of Primary Sclerosing Cholangitis (PSC), Primary Biliary Cholangitis (PBC), biliary atresia, and familial intrahepatic cholestasis type 3 (PFIC3).

3. The method according to claim 1, comprising administering a pharmaceutical composition comprising components (i) and (ii) and a pharmaceutically acceptable carrier.

4. The method according to claim 1, wherein components (i) and (ii) are administered sequentially.

5. The method according to claim 1, wherein components (i) and (ii) are administered separately.

6. The method according to claim 1, wherein components (i) and (ii) are administered simultaneously.

7. The method according to claim 1, wherein the cholestatic disease is PBC.

8. The method according to claim 1, wherein the cholestatic disease is PSC.

* * * * *